United States Patent
Sperl et al.

(10) Patent No.: US 9,014,333 B2
(45) Date of Patent: Apr. 21, 2015

(54) IMAGE RECONSTRUCTION METHODS FOR DIFFERENTIAL PHASE CONTRAST X-RAY IMAGING

(71) Applicant: General Electric Company, Schenectady, NY (US)

(72) Inventors: Jonathan Immanuel Sperl, Freising (DE); Dirk Beque, Munich (DE)

(73) Assignee: General Electric Company, Niskayuna, NY (US)

( * ) Notice: Subject to any disclaimer, the term of this patent is extended or adjusted under 35 U.S.C. 154(b) by 339 days.

(21) Appl. No.: 13/731,447

(22) Filed: Dec. 31, 2012

(65) Prior Publication Data

US 2014/0185757 A1    Jul. 3, 2014

(51) Int. Cl.

| | |
|---|---|
| A61B 6/04 | (2006.01) |
| G06T 5/10 | (2006.01) |
| G03B 42/02 | (2006.01) |
| G21K 1/06 | (2006.01) |
| A61B 6/00 | (2006.01) |
| G06T 7/00 | (2006.01) |
| G06T 11/00 | (2006.01) |
| G06T 5/00 | (2006.01) |

(52) U.S. Cl.
CPC .............. *A61B 6/484* (2013.01); *G06T 7/0012* (2013.01); *G06T 11/003* (2013.01); *G06T 5/001* (2013.01); *G06T 5/10* (2013.01); *G06T 2207/10116* (2013.01)

(58) Field of Classification Search
CPC .......... A61B 6/484; A61B 6/032; G21K 1/06; G03B 42/02; G03B 23/04; G03B 23/046; G06T 5/10

USPC .................... 378/62, 145, 36, 157, 158, 132; 382/254
See application file for complete search history.

(56) References Cited

U.S. PATENT DOCUMENTS

| | | | |
|---|---|---|---|
| 4,845,352 A | | 7/1989 | Benschop |
| 6,094,260 A | * | 7/2000 | Rockstroh et al. ........... 356/35.5 |
| 7,433,444 B2 | | 10/2008 | Baumann et al. |
| 7,440,542 B2 | | 10/2008 | Baumann et al. |

(Continued)

FOREIGN PATENT DOCUMENTS

| | | |
|---|---|---|
| DE | 102009018882 A1 | 10/2010 |
| WO | 2007074029 A1 | 7/2007 |

(Continued)

OTHER PUBLICATIONS

Thuring, Thomas et al.; "Non-linear regularized phase retrieval for unidirectional X-ray differential phase contrast radiography;" Optics Express 25545, vol. 19, No. 25; Dec. 5, 2011, 14 pages.

*Primary Examiner* — David A Vanore
(74) *Attorney, Agent, or Firm* — Robert M. McCarthy

(57) ABSTRACT

An image reconstruction method for differential phase contrast imaging includes receiving data corresponding to a signal produced by an X-ray detector and corresponding to X-rays that passed through a subject and a grating system to reach the X-ray detector. The method also includes performing a fringe analysis on the received data. The fringe analysis includes a non-integer fringe fraction correction utilizing one or more adapted basis functions in the Fourier domain to determine one or more Fourier coefficients. A differential phase image of the subject is generated by utilizing the one or more Fourier coefficients.

20 Claims, 12 Drawing Sheets

(56) References Cited

U.S. PATENT DOCUMENTS

| | | |
|---|---|---|
| 7,453,981 B2 | 11/2008 | Baumann et al. |
| 7,486,770 B2 | 2/2009 | Baumann et al. |
| 7,492,871 B2 | 2/2009 | Popescu et al. |
| 7,522,698 B2 | 4/2009 | Popescu et al. |
| 7,522,708 B2 * | 4/2009 | Heismann et al. ............ 378/145 |
| 7,532,704 B2 * | 5/2009 | Hempel .......................... 378/19 |
| 7,535,986 B2 * | 5/2009 | Hempel ............................ 378/4 |
| 7,564,941 B2 | 7/2009 | Baumann et al. |
| 7,639,786 B2 | 12/2009 | Baumann et al. |
| 7,645,018 B2 | 1/2010 | Ikushima |
| 7,646,843 B2 | 1/2010 | Popescu et al. |
| 7,653,177 B2 | 1/2010 | Baumann et al. |
| 7,889,838 B2 | 2/2011 | David et al. |
| 7,920,673 B2 | 4/2011 | Lanza et al. |
| 7,924,973 B2 | 4/2011 | Kottler et al. |
| 7,949,095 B2 | 5/2011 | Ning et al. |
| 7,983,381 B2 | 7/2011 | David et al. |
| 8,005,185 B2 * | 8/2011 | Popescu .......................... 378/36 |
| 8,009,796 B2 | 8/2011 | Popescu |
| 8,103,329 B2 * | 1/2012 | Fomitchov et al. ............ 600/407 |
| 8,165,270 B2 | 4/2012 | David |
| 8,233,587 B2 | 7/2012 | Sato |
| 8,243,879 B2 | 8/2012 | Itoh |
| 8,306,183 B2 * | 11/2012 | Koehler ........................... 378/36 |
| 8,351,570 B2 | 1/2013 | Nakamura |
| 8,374,309 B2 * | 2/2013 | Donath et al. .................. 378/19 |
| 8,520,217 B2 | 8/2013 | Naoi |
| 2011/0013743 A1 | 1/2011 | Nakamura |
| 2011/0051889 A1 | 3/2011 | Sato |
| 2012/0099702 A1 * | 4/2012 | Engel et al. ..................... 378/62 |
| 2013/0130182 A1 * | 5/2013 | Markle et al. ................. 430/322 |
| 2014/0169524 A1 * | 6/2014 | Sperl et al. ...................... 378/62 |
| 2014/0185757 A1 * | 7/2014 | Sperl et al. ...................... 378/62 |

FOREIGN PATENT DOCUMENTS

| | | |
|---|---|---|
| WO | 2010150136 A1 | 12/2010 |
| WO | 2011011014 A1 | 1/2011 |
| WO | 2012029039 A1 | 3/2012 |

* cited by examiner

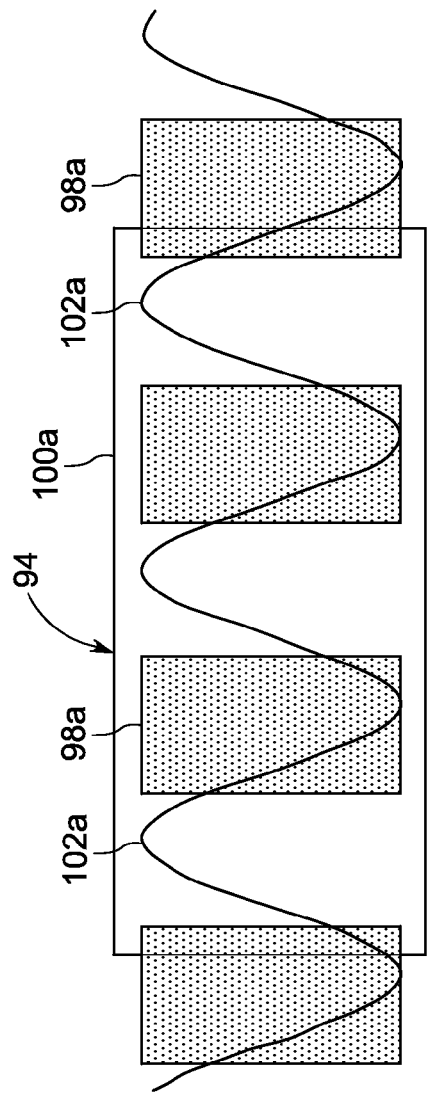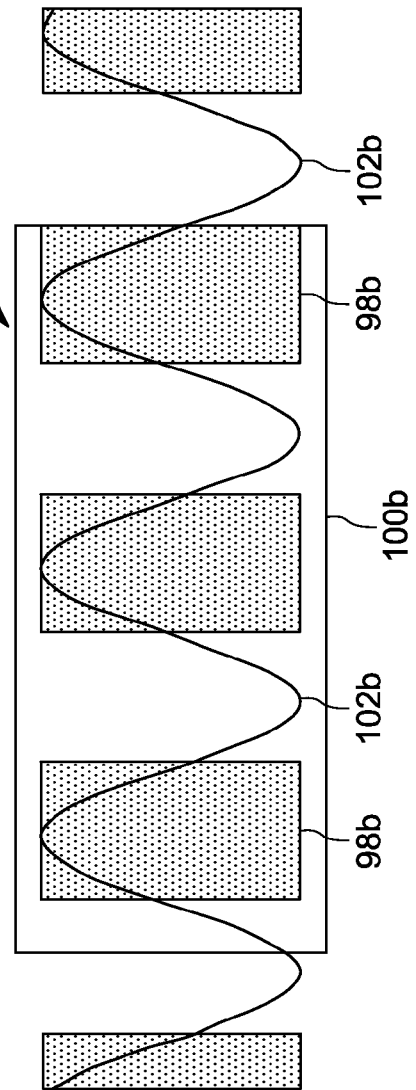
FIG. 4A
FIG. 4B

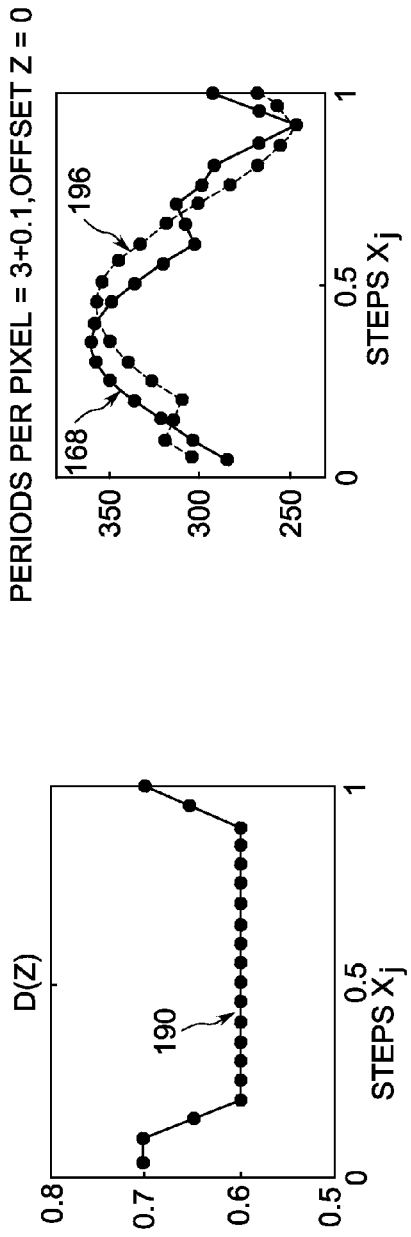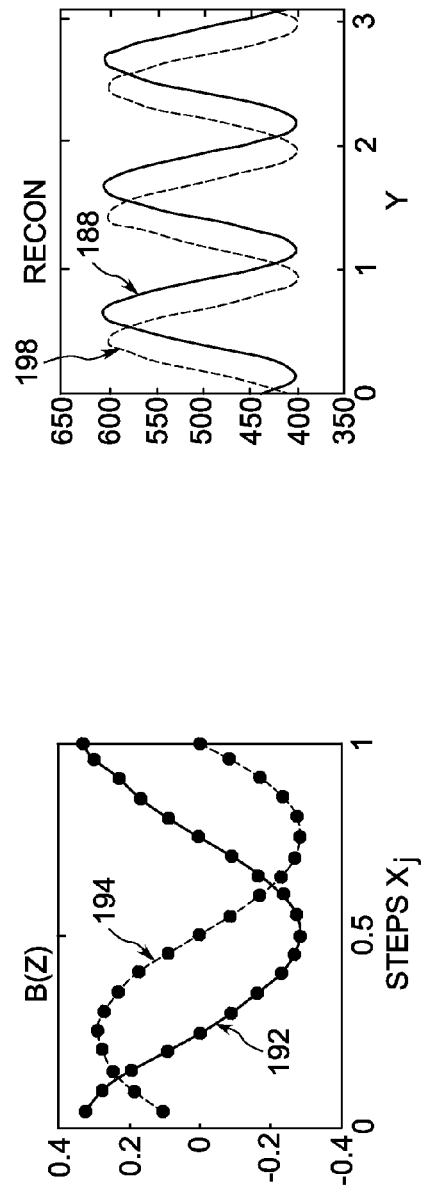

IMAGE RECONSTRUCTION METHODS FOR DIFFERENTIAL PHASE CONTRAST X-RAY IMAGING

BACKGROUND

The subject matter disclosed herein generally relates to X-ray imaging techniques and, in particular, to systems and methods for reconstructing images in X-ray phase contrast imaging.

In non-invasive imaging systems, X-ray tubes are used in various X-ray systems and computed tomography (CT) systems as a source of X-ray radiation. The radiation is emitted in response to control signals during an examination or imaging sequence. Typically, the X-ray tube includes a cathode and an anode. An emitter within the cathode may emit a stream of electrons in response to heat resulting from an applied electrical current, and/or an electric field resulting from an applied voltage to a properly shaped metallic plate in front of the emitter. The anode may include a target that is impacted by the stream of electrons. The target may, as a result of impact by the electron beam, produce X-ray radiation to be emitted toward an imaged volume.

Conventional X-ray imaging systems may detect an imaged volume based on absorption of the X-ray radiation. However, absorption-based techniques may provide images with insufficient distinction between certain types of tissue structures. For example, tumors and fluid-filled cysts may be difficult to distinguish on images generated by X-ray absorption of tissue. Other techniques, such as phase contrast techniques, may provide images with more contrast between different types of tissue structures. However, image reconstruction associated with such techniques may be subject to a variety of drawbacks associated with factors such as image geometry, hardware constraints, and so forth. For example, in instances in which the length of a pixel on the X-ray detector is not an integer of a fringe or interference period, the image reconstruction process may yield inaccurate or non-optimal results.

BRIEF DESCRIPTION

In one embodiment, a method for correcting for non-integer fringe fractions in differential phase contrast imaging includes receiving data corresponding to a measured signal. The measured signal corresponds to an X-ray signal detected by a detector after passing through a subject located with a grating arrangement between an X-ray source and the detector. The method also includes determining a basis function in the Fourier domain based on an initial offset value, fitting the data corresponding to the measured signal to the basis function, determining an adapted basis function in the Fourier domain based on a shifted offset value, and fitting the data corresponding to the measured signal to the adapted basis function.

In another embodiment, an X-ray imaging system for differential phase contrast imaging of a subject includes an X-ray source that in operation generates an X-ray beam directed toward the subject, a detector that in operation detects at least a portion of the X-ray beam and produces a signal corresponding to the detected portion of the X-ray beam, and a grating system having a source grating located between the X-ray source and the subject, and a phase grating and an analyzer grating each located between the subject and the detector. A controller in operation receives the signal from the detector and performs a reconstruction of a phase image of the subject based on the signal. The reconstruction includes a fringe analysis in which the controller performs a non-integer fringe fraction correction utilizing one or more adapted basis functions in the Fourier domain.

In another embodiment, an image reconstruction method for differential phase contrast imaging includes receiving data corresponding to a signal produced by an X-ray detector and corresponding to X-rays that passed through a subject and a grating system to reach the X-ray detector. The method also includes performing a fringe analysis on the received data. The fringe analysis includes a non-integer fringe fraction correction utilizing one or more adapted basis functions in the Fourier domain to determine one or more Fourier coefficients. A differential phase image of the subject is generated by utilizing the one or more Fourier coefficients.

In another embodiment, a non-transitory computer readable medium encodes one or more executable routines, which, when executed by a processor, cause the processor to perform acts including performing an image reconstruction of a phase image of a subject based on a signal generated by an X-ray detector based on a detected X-ray beam that passed through a subject and a grating system. Performing the image reconstruction includes a fringe analysis utilizing one or more adapted basis functions in the Fourier domain for a non-integer fringe fraction correction.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 4A is a schematic illustrating an example of a fringe pattern that may be obtained in an embodiment of a phase contrast X-ray imaging operation;

FIG. 4B is a schematic illustrating an example of a fringe pattern that may be obtained in an embodiment of a phase contrast X-ray imaging operation;

FIGS. 11A-D illustrate graphs corresponding to a second iteration of an embodiment of an offset stepping procedure.

DETAILED DESCRIPTION

Provided herein are fringe analysis systems and methods for differential X-ray phase contrast (XPC) imaging that enable a phase image of a subject to be generated from acquired data. In many differential XPC systems, data corresponding to the convolution of an acquired signal and an appropriate grating function is obtained and analyzed during image reconstruction. More particularly, an offset, amplitude, and phase of the acquired curve may be determined during reconstruction. Presently disclosed embodiments provide for curve characterization while taking into account non-integer multiples of fringe periods per detector pixel. That is, certain embodiments provided herein may enable characterization of the effect of non-integer fractions as well as correction for these effects. For example, in some embodiments, modified basis functions in the Fourier domain may be utilized to provide a correction in instances where the measured fringes are not a convolution of the fringes and the grating (i.e., not sinusoids), for instance, due to the length of the detector pixel not being an integer multiple of the fringe period. These and other features of presently disclosed embodiments are described in more detail below.

Figure 1:
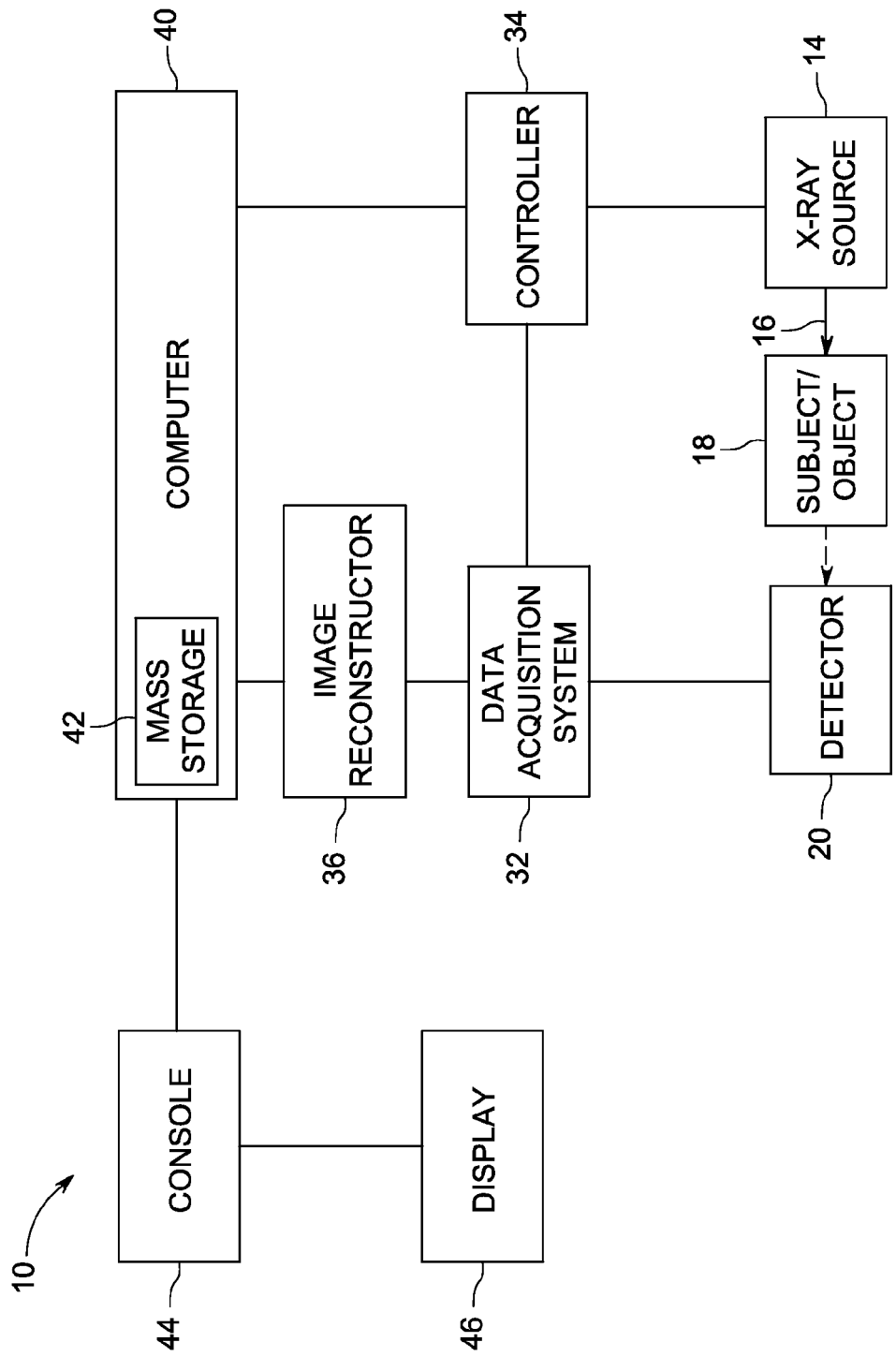
FIG. 1 is a block diagram illustrating an embodiment of an X-ray imaging system.

Turning now to the drawings, FIG. 1 illustrates an X-ray imaging system 10 including an X-ray source 14 that projects a beam of X-rays 16 through a subject 18 (e.g., a patient, object, sample, etc.) toward one or more detectors 20. The detector 20 is coupled to a data acquisition system 32. The one or more detectors 20 sense the transmitted X-rays that pass through the subject 18, and the data acquisition system 32 converts the sensed X rays to digital signals for subsequent processing. Each detector 20 produces an electrical signal that represents the intensity of an impinging X-ray beam after it passes through the subject 18. The operation of the X-ray source 14 may be governed by an X-ray controller 34 that provides power and timing signals to the X-ray source 14. An image reconstructor 36 receives sampled and digitized X-ray data from the data acquisition system 32 and performs reconstructions to produce phase contrast images. The reconstructed image is applied as an input to a processor-based computer 40 that stores the image in a mass storage device 42.

The computer 40 also receives commands and scanning parameters from an operator via a console 44 that has some form of operator interface, such as a keyboard, mouse, voice activated controller, or any other suitable input apparatus. An associated display 46 enables the operator to observe the reconstructed images and other data from the computer 40. The operator-supplied commands and parameters are used by the computer 40 to provide control signals and information to the data acquisition system 32 and the X-ray controller 34.

Figure 2:
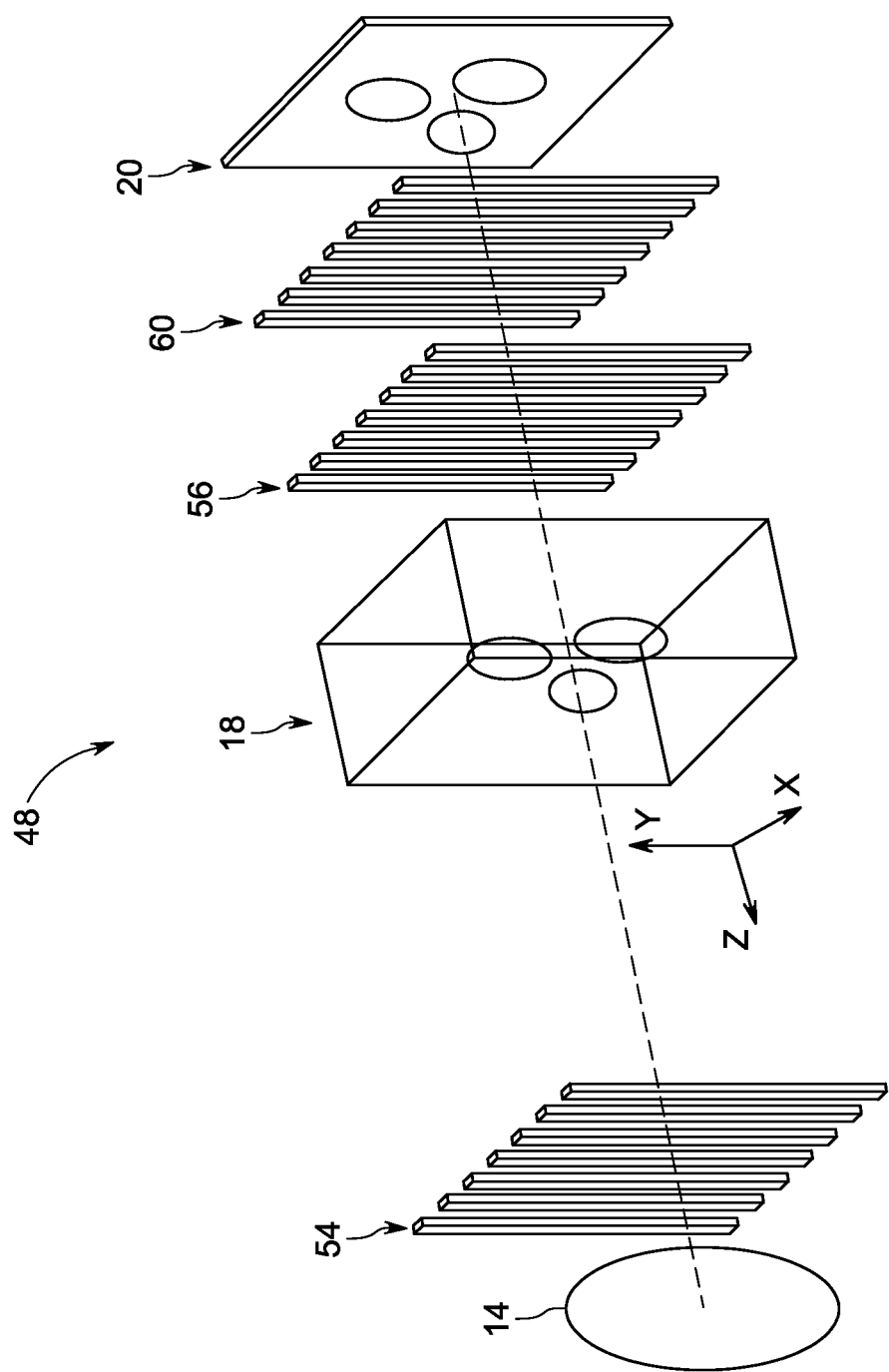
FIG. 2 is a schematic illustrating an example X-ray beam path in a phase contrast imaging operation in accordance with an embodiment.

FIG. 2 illustrates a differential XPC imaging setup 48 in which a spatially coherent X-ray beam is used to probe an object (or subject) 18. In the illustrated embodiment, an incoherent X-ray source 14 is provided with a blocking grating 54 to create the coherent X-ray beam. However, in other arrangements, the spatially coherent X-ray beam may be realized by synchrotron radiation, a micro focus X-ray source, or any other suitable source. In the illustrated embodiment, the spatially coherent X-ray beam passes a phase grating 56, and periodic interference patterns or fringes are generated. Since their period is typically in the order of a few μm, an interferometric technique is applied to analyze the fringes using an X-ray detector 20 (e.g., having a pixel in the order of a few 100 μm). Another blocking grating 60 having the same period as the fringes is placed in front of the detector 20.

During operation of the illustrated imaging setup 48, in a series of steps, grating 60 is shifted by a fraction of its period in the direction orthogonal to the grating slits, and images are taken for each position. After covering the entire period, the measurements for each detector pixel may be described as the convolution of the fringes with the rectangular grating function. Using Fourier analysis, the phase of the fringes are determined During an imaging operation, in addition to the gratings 56 and 60, the object or subject 18 is placed into the X-ray beam, and the X-rays are refracted by the object 18 and hence undergo an additional phase shift. By repeating the measurement procedure, the phase of the shifted fringes is detected and the difference of both measurements yields the phase shift due to the object 18. In other words, the differential XPC measurement generates projections of the gradient of the cumulative phase shift due to refractive index variability of the object in a direction orthogonal to the X-ray beam and to the grating slits.

Figure 3:
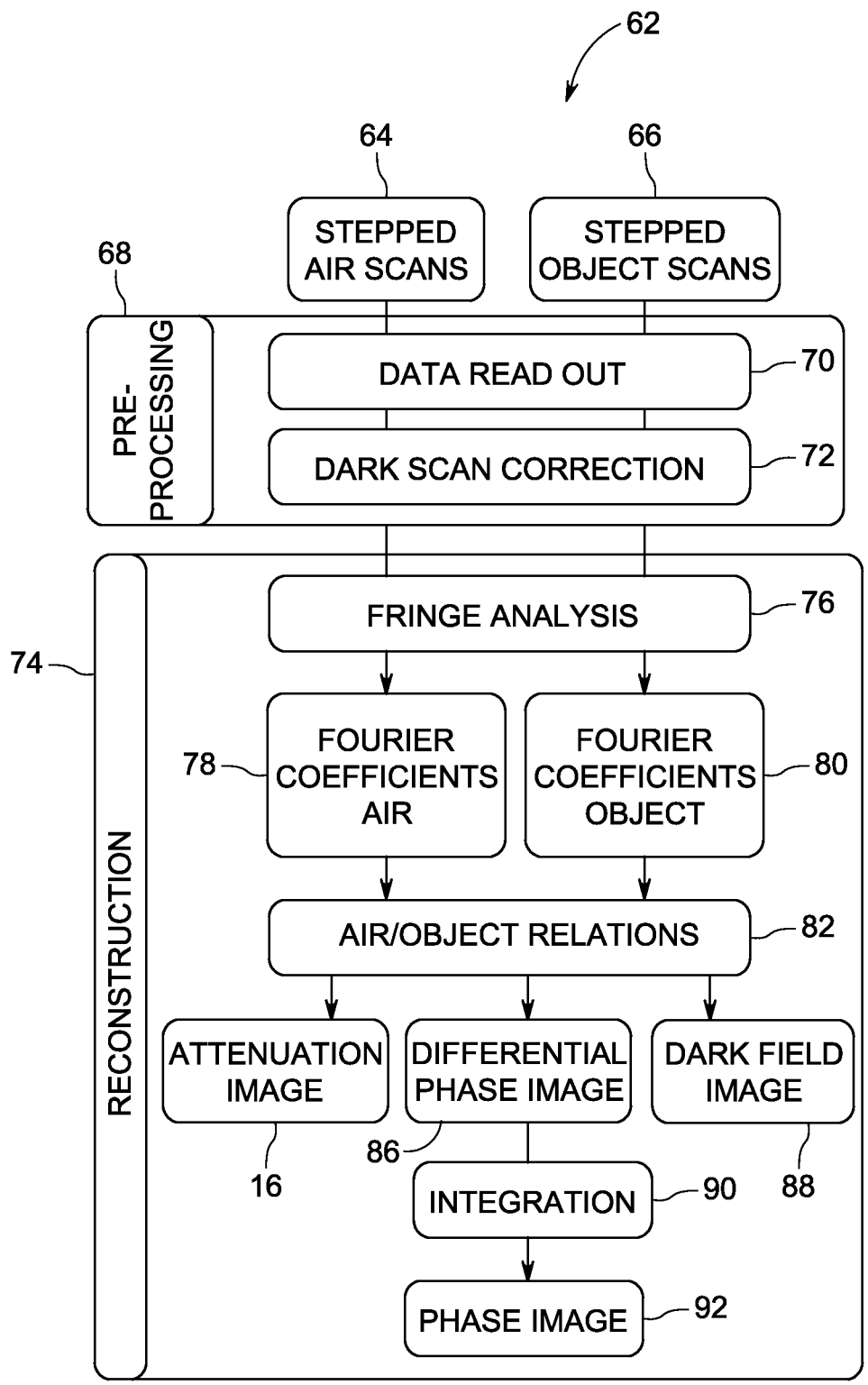
FIG. 3 is a block diagram illustrating an embodiment of an image reconstruction process for a phase contrast X-ray imaging operation.

Once measured signals are obtained in this manner, data processing and reconstruction of phase images may be performed to obtain diagnostically useful images. FIG. 3 illustrates an embodiment of a method 62 that may be employed, for example, by controller 34 or image reconstructor 36, to obtain one or more images of the object 18. More specifically, the method 62 calls for one or more stepped air scans 64 and one or more stepped object scans 66 to be performed, for example, in accordance with the steps described above with respect to the imaging setup 48. During pre-processing 68, the data obtained from the scans 64 and 66 is read out (block 70), and a dark scan correction is performed (block 72) to normalize for the noise introduced into the system by features of the detector 20.

During image reconstruction 74, the data corresponding to the signals measured by the detector is processed to obtain the desired images. In the illustrated embodiment, a fringe analysis (block 76) is performed to process the interference patterns generated during the imaging procedure when the X-rays interacted with the object 18 and the gratings 56 and 60. For example, since the measurement signal represents the convolution of the generated signal with the grating function, characterization of the obtained curve is performed to determine the offset, amplitude, and phase. A variety of implementation-specific steps may occur during the fringe analysis, such as but not limited to computation of the zeroth and first order Fourier coefficients. In some embodiments, the fringe analysis 76 may include a correction for the effect of non-integer fringe fractions on the measurement signal. As described in more detail below, this correction may include the use of modified basis functions in the Fourier domain.

The fringe analysis (block 76) outputs include Fourier coefficients 78 corresponding to the air scans 64 and Fourier coefficients 80 corresponding to the object scans 66. In the illustrated embodiment, the Fourier coefficients 78 and 80 are then used to perform an air/object relation step (block 82) in which features of the air scan 64 are compared to features of the object scan 66 to obtain clinically relevant information. That is, the data from the air scan 64 may be used as a baseline for comparison with the data from the object scan 66 to determine the phase shift contributed by the object 18. Accordingly, an attenuation image 84, a differential phase image 86, and a dark field image 88 are produced in the depicted image reconstruction 74. However, it should be noted that in other embodiments, only select images may be produced, depending on implementation-specific considerations. Further, in order to visualize the differential XPC projections in a manner that is in accordance with conventional diagnostics, it may be desirable to integrate the differential phase image 86 (block 90) to generate a phase image 92 of the imaged object 18.

As noted above, in a typical fringe analysis, the sinusoidal fringes s(x) with period p are measured indirectly by stepping the grating g(x), which has the same period, in direction x. That is, for the j-th step, the grating is shifted by the distance $x_j$ ($x_1$=(j−1)/J∈[0,1] with J the total number of steps for a one dimensional convolution). For L=N+h, N∈ℕ, h∈[0,1], being the length of detector pixel in x-direction, one measures $$f_j = \int_0^L g(x-x_j) s(x) dx, j=1,\ldots,J \quad (1)$$

and if L is an integer multiple of p (i.e., h=0), it can be written $$f_j = N\int_0^1 g(x-x_j)s(x)dx = N(g*s)(x_j) \quad (2)$$

because g and s are both p-periodic. By computing the zeroth and first order Fourier coefficients of $f=(f_1,\ldots,f_J)^T$, i.e., $$\tilde{c}_0 = \mathcal{F}(f)_0 \text{ and } \tilde{c}_1 = \mathcal{F}(f)_1 \quad (3)$$

Whereas $\mathcal{F}(f)_n = \frac{1}{j}\sum_j f(x_j)e(nx_j)$ and $e(x) := \exp(-2\pi i x)$.

the Fourier coefficients of s are $$c_n = \mathcal{F}(s)_n = \frac{1}{N\mathcal{F}(g)_n}\tilde{c}_n, \quad (4)$$

$$n = 1, 2, \ldots$$

due to the Fourier relationship $$\mathcal{F}(f)_n = \mathcal{F}(Ng*s)_n = N\mathcal{F}(g)_n\mathcal{F}(s)_n. \quad (5)$$

Given the Fourier coefficients, the offset $a_0$, the amplitude $a_1$, and the phase φ of the sinusoid may be determined:

$$s(x) = a_0 + a_1 \cos(2\pi x + \phi) \quad (6)$$

as $a_0 = c_0$, $a_1 = 2\text{abs}(c_1)$, φ=arg($c_1$)
where abs(•) and arg(●) denote the magnitude and the phase of a complex number, respectively.

That is, a traditional fringe analysis does not take into account that the measured fringes are not a convolution of the fringes and the grating function in instances in which the length of the detector pixel is not an integer multiple of the fringe period. FIGS. 4A and 4B schematically illustrate this non-integer fringe fraction (NIF) effect. In the schematics 94 and 96, there is not a constant integer number of grating slots overlapping with the detector for the different steps and, thus, a correction is warranted. For example, FIG. 4A illustrates that for various steps of a grating 98a, a detector 100a measures different sections of the fringes 102a, and FIG. 4B illustrates that for various steps of a grating 98b, a detector 100b measures different sections of the fringes 102b. In schematic 94, three complete sections of the fringes 102a are measured, whereas in schematic 96, only approximately 2.35 grating slots match the detector 100b. As illustrated in FIGS. 4A and 4B, there is not a constant integer number of grating slots overlapping with the detector for the different steps, thus leading to the NIF effect.

Figure 5A:
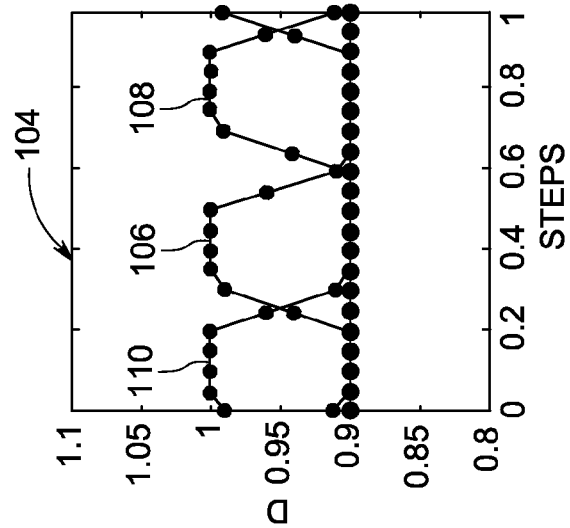
FIG. 5A is a Fourier coefficient graph in accordance with an embodiment.
Figure 5B:
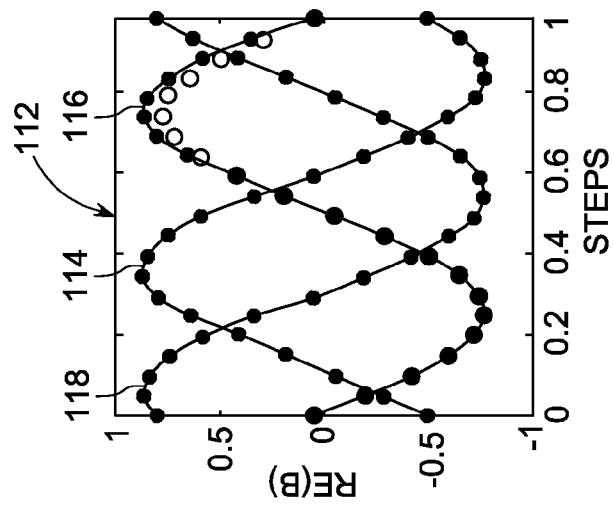
FIG. 5B is a Fourier coefficient graph illustrating a real part of the Fourier coefficient in accordance with an embodiment.
Figure 5C:
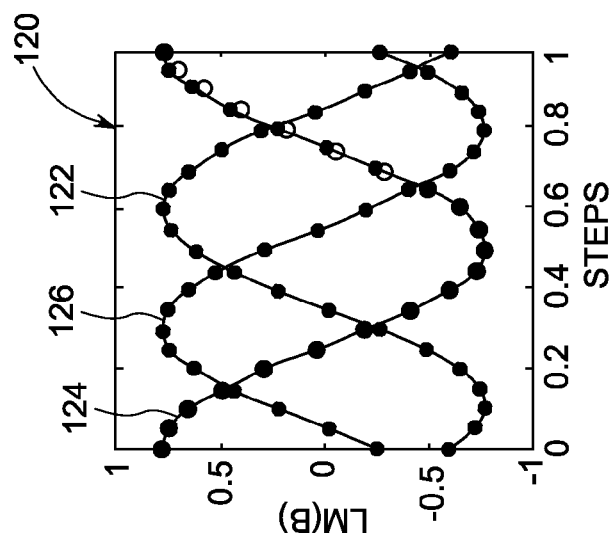
FIG. 5C is a Fourier coefficient graph illustrating an imaginary part of the Fourier coefficient in accordance with an embodiment.

For a mathematical description of the problem, s can be formulated as a complex harmonic function. That is, $$s(x) = a_0 + a_1 \cos(2\pi x + \phi) = c_0 + c_1 e(x) \quad (7)$$

and this can be inserted into (1):

$$f_j = \int_0^L g(x-x_j-z_0)(c_0+c_1 e(x))dx = c_0\int_0^L g(x-x_j-z_0)dx + c_1\int_0^L g(x-x_j-z_0)e(x)dx \quad (8)$$

where $\int_0^L g(x-x_j-z_0)dx =: d_j(z_0)$ and $\int_0^L g(x-x_j-z_0)e(x)dx =: b_j(z_0)$ whereas $z_0 \in [-\frac{1}{2}, \frac{1}{2}]$ denotes the offset of the grating with respect to the detector. The offset has been omitted in the considerations above regarding the case h=0, as it cancels out for the relative comparison of two signals. However, this is not the case for h is not equal to 0. For a standard rectangular grating, $$g(x) = \begin{cases} 0 & \text{if } x \in k + [0, w], k \in \mathbb{Z} \\ 1 & \text{else} \end{cases} \quad (9)$$

with dutycycle w∈(0,1), FIGS. 5A-C illustrate the coefficients d and b. For h=0, d and b become scaled and shifted Fourier bases again, i.e., $$d_j(z_0) = N\mathcal{F}(g)_0, \; b_j(z_0) = N\mathcal{F}(g)_1 e(x_j+z_0). \quad (10)$$

More specifically, a graph 104 shown in FIG. 5A illustrates coefficient d for a rectangular grating (duty cycle w=0.3) in which L=3.1, J=20, and $z_0$=−0.4, −0.1, and +0.2 for plots 106, 108, and 110, respectively, and the open circles illustrate the coefficients for L=3.0 and $z_0$=+0.2. Similarly, a graph 112 shown in FIG. 5B illustrates the real part of coefficient b for a rectangular grating (duty cycle w=0.3) in which L=3.1, J=20, and $z_0$=−0.4, −0.1, and +0.2 for plots 114, 116, and 118, respectively, and the open circles illustrate the coefficients for L=3.0 and $z_0$=+0.2. Likewise, a graph 120 shown in FIG. 5C illustrates the imaginary part of coefficient b for a rectangular grating (duty cycle w=0.3) in which L=3.1, J=20, and $z_0$=−0.4, −0.1, and +0.2 for plots 122, 124, and 126, respectively, and the open circles illustrate the coefficients for L=3.0 and $z_0$=+0.2.

Figure 6C:
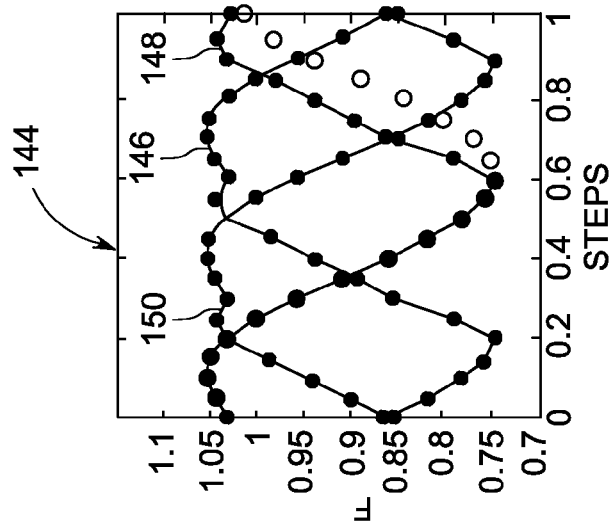
FIGS. 6A-C are graphs illustrating simulated measured signals in accordance with disclosed embodiments.
Figure 6B:
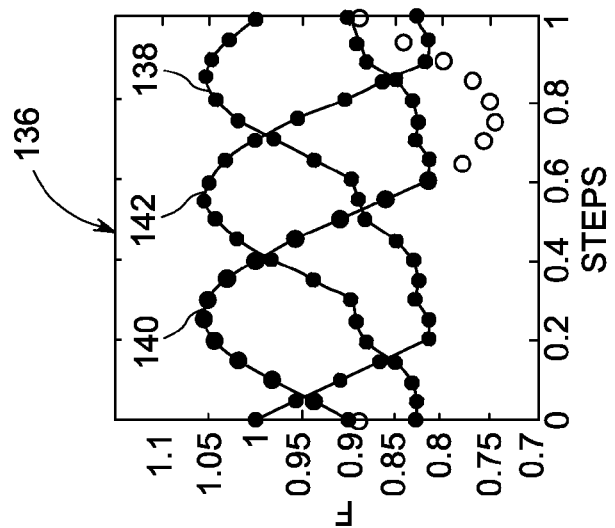
Figure 6A:
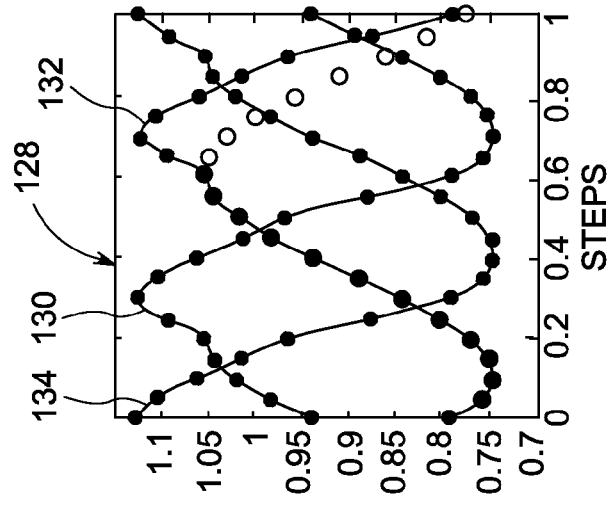

Based on the coefficients b and d, the signal f that would be measured for an ideal input signal s can be simulated. This is illustrated, for example, in FIGS. 6A-C. As before, for each of FIGS. 6A-C, the open circles illustrate the coefficients for L=3.0 and $z_0$=+0.2. A graph 128 shown in FIG. 6A shows a simulated NIF affected measurement f for $a_0$=1, $a_1$=0.2, φ=0.3π for a rectangular grating (duty cycle w=0.3) in which L=3.1, J=20, and $z_0$=−0.4, −0.1, and +0.2 for plots 130, 132, and 134, respectively. Similarly, graph 136 shown in FIG. 6B shows a simulated NIF affected measurement f for $a_0$=1, $a_1$=0.2, φ=1.0π for a rectangular grating (duty cycle w=0.3) in which L=3.1, J=20, and $z_0$=−0.4, −0.1, and +0.2 for plots 138, 140, and 142, respectively. Likewise, graph 144 shown in FIG. 6C shows a simulated NIF affected measurement f for $a_0$=1, $a_1$=0.2, φ=1.0π for a rectangular grating (duty cycle w=0.3) in which L=3.1, J=20, and $z_0$=−0.4, −0.1, and +0.2 for plots 146, 148, and 150, respectively.

As shown, deviations from a sinusoid are observed, and the appearance of the NIF effect depends on the phase of the signal. It should also be noted that the effect would become less dominant for a larger N, i.e., more periods per pixel, since the relative difference between the high and the low state of d becomes smaller. Also the distortion of the phase would become less severe for a higher visibility, i.e., a larger ratio $a_1/a_0$, since the NIF effect on the phase is less pronounced for b than for d.

From the simulations shown above, it can be seen that the standard Fourier reconstruction would become erroneous for h=0. This would affect all coefficients, the offset $a_0$, the amplitude $a_1$, and the phase. A quantitative analysis will be shown below. Therefore, provided herein are embodiments of a novel reconstruction technique that enables correction for NIF effects.

In a first step, it is assumed that the grating offset $z_0$ is known. Based on (8), the reconstruction may be rewritten as an optimization task: For $c=[C_0,c_1]^T$, $d(z_0)=(d_1(z_0), \ldots, d_j(z_0))^T$, $b(z_0)=(b_1(z_0), \ldots, b_1(z_0))^T$, set $A(z_0)=[d(z_0), b(z_0)]$ and formulate the linear least-squares-minimization:

$$\min_c \|A(z_0)c-f\|. \quad (11)$$

The solution can be computed analytically by solving the linear equation system $$(A(z_0)^H A(z_0))c = A(z_0)^H f \quad (12)$$

yielding proper Fourier coefficients $c_0$ and $c_1$. It should be noted that for h=0, this method coincidents with the direct computation of the Fourier coefficients, since $$A(z_0)^H A(z_0) = \begin{bmatrix} N^2 \mathcal{F}(g)_0^2 J & 0 \\ 0 & N^2 \mathcal{F}(g)_1^2 J \end{bmatrix}, \quad (13)$$

$$A(z_0)^H f = \begin{bmatrix} N\mathcal{F}(g)_0 \sum_j f_j \\ N\mathcal{F}(g)_1 \sum_j f_j e(x_j + z_0) \end{bmatrix}$$

whereas the offset $z_0$ causes a constant phase shift.

In practice, $z_0$ might be unknown. In principle, one could treat $z_0$ as another optimization variable. However, in this case, the optimization task would become non-linear with a non-convex residuum (see below) and might be hard to solve in a robust manner. Accordingly, presently disclosed embodiments utilize an adaptive offset stepping approach to estimate $z_0$ based on a low-noise calibration scan. In more detail, this means that (12) is solved for various sample values $z_k \in [-\frac{1}{2}, \frac{1}{2}]$, $k=1, \ldots, K$, the minimum residual norm is determined accordingly to the following equation:

$$\min_k \{\min_c \|A(z_k)c-f\|\} \quad (14)$$

and this is adaptively repeated with a finer sampling in a neighborhood of the identified $z_k$.

Figure 7:
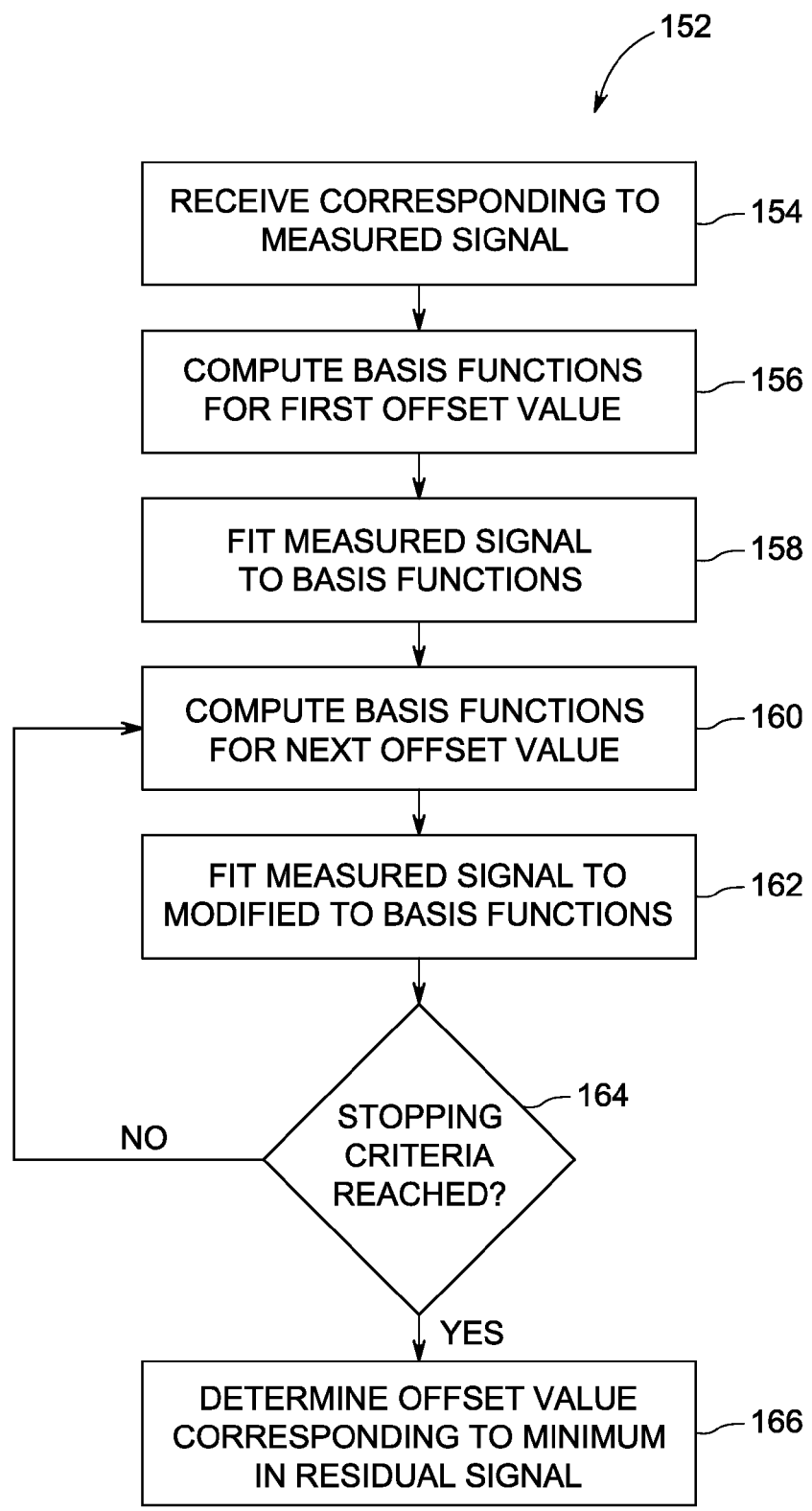
FIG. 7 illustrates an embodiment of a method for correcting for non-integer fringe fractions during an image reconstruction.

This adaptive offset stepping approach may be utilized to correct for the NIF effect. FIG. 7 illustrates a flow chart of a method 152 suitable for use by a controller for performing this correction in accordance with the above equations. The method 152 includes the steps of receiving data corresponding to a measured signal (block 154) and computing basis functions for a first offset value (block 156). The measured signal is then fit to the basis functions (block 158) and basis functions for the next offset value are then computed (block 160). The measured signal is then fit to the modified basis functions (block 162) and an inquiry is made as to whether a stopping criteria (e.g., the last offset value is reached) is reached (block 164). If the stopping criteria has not been reached, the process continues. If the stopping criteria has been reached, the method 152 proceeds with a determination of the offset value corresponding to a minimum in the residual signal (block 166).

Figure 8:
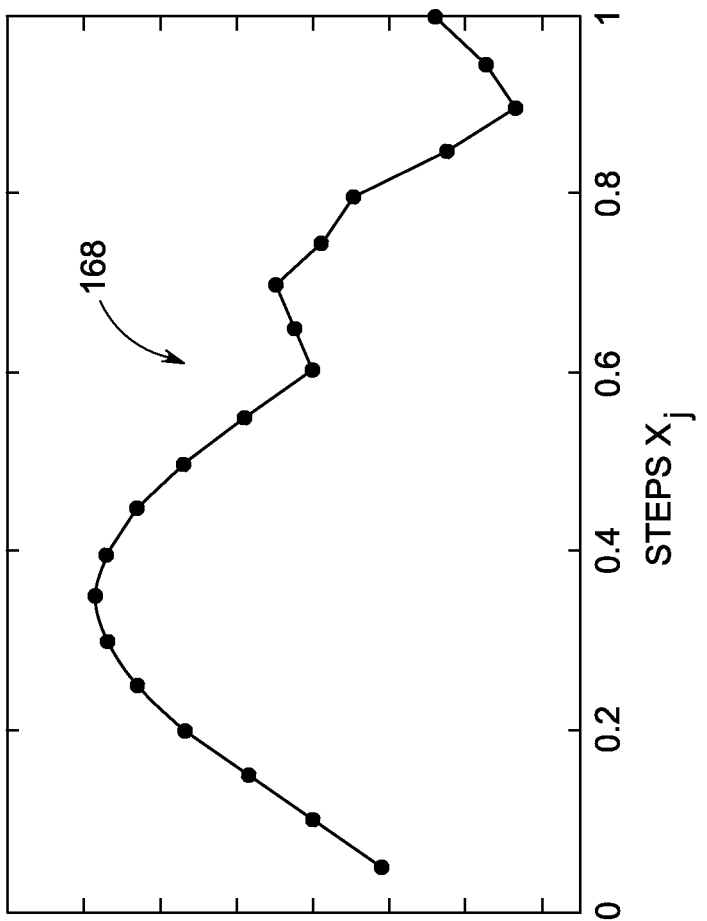
FIG. 8 is a graph of a simulated measured signal in accordance with an embodiment.
Figure 9:
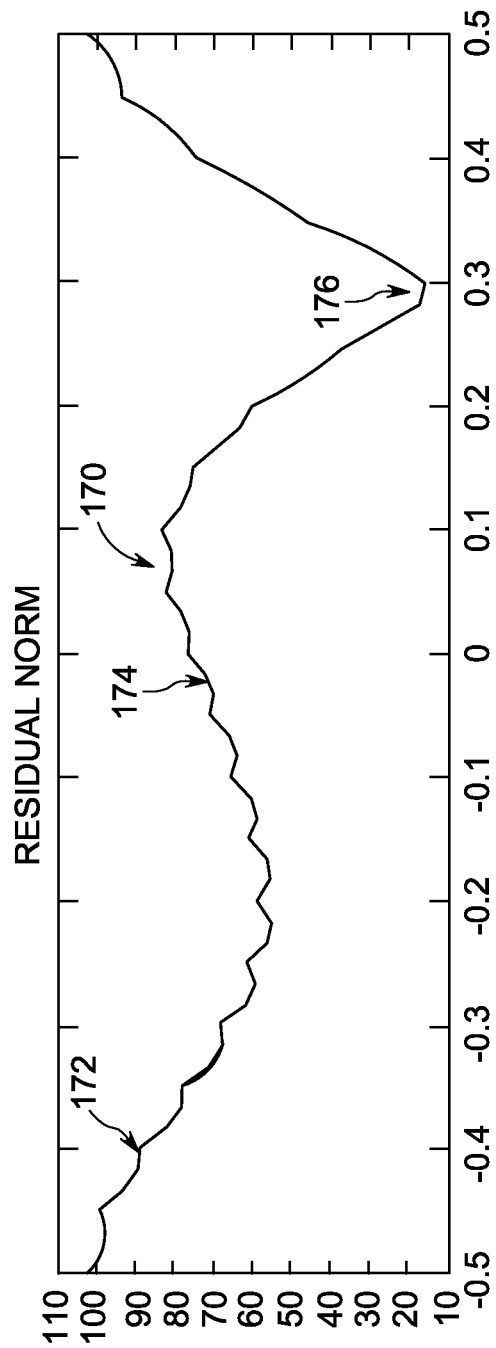
FIG. 9 is a graph of a residual norm plot in accordance with an embodiment.

An example application of the adaptive offset stepping method 152 of FIG. 7 is shown in FIGS. 8, 9, 10A-D, 11A-D, and 12A-D. However, it should be noted that the illustrated iterations are merely examples of a few of a plurality of likely iterations performed in one embodiment and are not meant to limit presently disclosed embodiments. Specifically, FIG. 8 illustrates an example of a measured signal 168 experiencing NIF effects and being in need of NIF correction. That is, while measured signal 168 would be expected to have a sinusoidal shape, NIF effects have distorted the signal in the depicted manner. FIG. 9 illustrates an example residual norm 170 corresponding to the measured signal 168. That is, by using equations (12) and (14), presently disclosed embodiments of the adaptive offset stepping approach may be utilized to identify the z value corresponding to the absolute minimum of the residual norm. FIGS. 10A-D, 11A-D, and 12A-D illustrate example iterations of one embodiment of the adaptive offset stepping approach for iterations corresponding to example locations 172, 174, and 176 along the residual norm plot of FIG. 9.

Figure 10C:
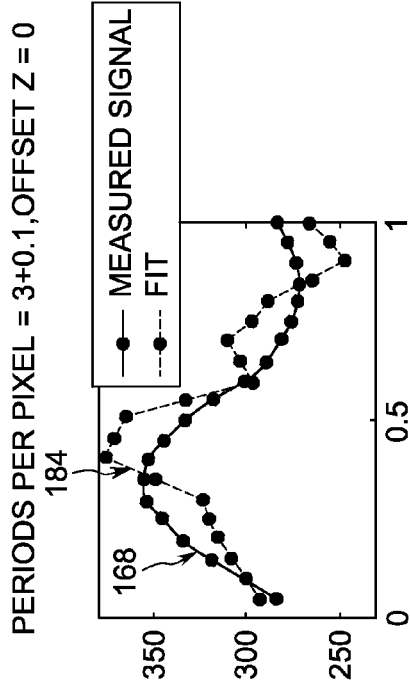
FIGS. 10A-D illustrate graphs corresponding to a first iteration of an embodiment of an offset stepping procedure.
Figure 10D:
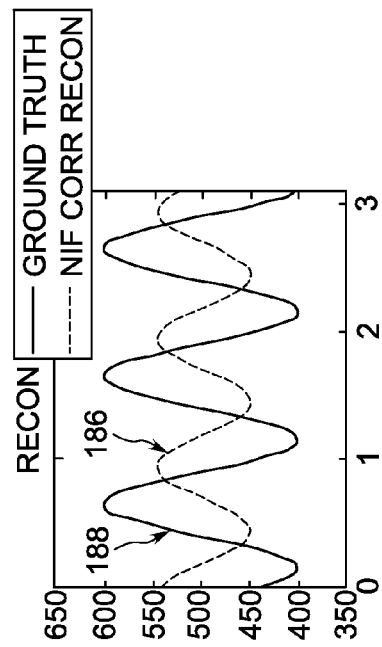
Figure 10A:
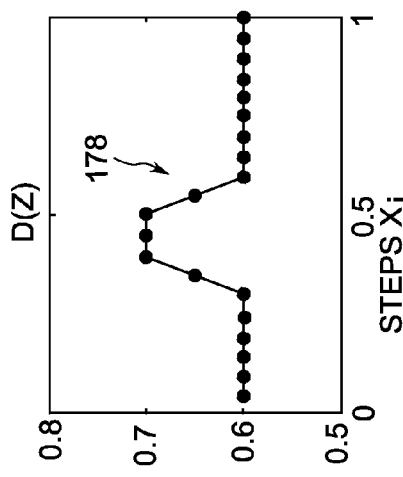
Figure 10B:
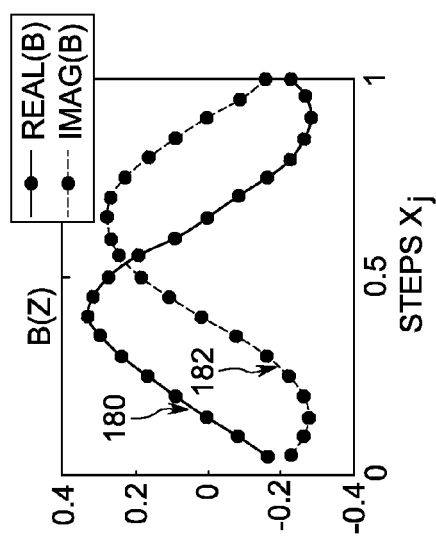

Specifically, FIG. 10A illustrates a plot 178 of the basis function d for the z value corresponding to location 172 on the residual norm. FIG. 10B illustrates plots 180 and 182 of the real and imaginary parts of the basis function b, respectively, for the z value corresponding to location 172 on the residual norm. FIG. 10C illustrates the measured signal 168 and a computed fit 184 utilized to generate a NIF corrected reconstruction 186 that can be compared to the ground truth 188 in FIG. 10D. That is, for the offset value corresponding to location 172 on the residual norm 170, modified basis functions are determined (e.g., as in FIGS. 10A and 10B), and the modified basis functions are used for fitting (e.g., as in FIG. 10C) and the reconstruction (e.g., as in FIG. 10D).

This process is repeated for several iterations until the entire available space has been sampled, for example, to ensure that the absolute minimum (and not a local minimum) of the residual norm has been identified. For example, this process is again repeated for the offset value corresponding to location 174 on the residual norm 170, as shown in FIGS. 11A-D. Here again, FIG. 11A illustrates a plot 190 of the basis function d for the z value corresponding to location 174 on the residual norm. FIG. 11B illustrates plots 192 and 194 of the real and imaginary parts of the basis function b, respectively, for the z value corresponding to location 174 on the residual norm. FIG. 11C illustrates the measured signal 168 and a computed fit 196 utilized to generate a NIF corrected reconstruction 198 that can be compared to the ground truth 188 in FIG. 11D. As before, for the offset value corresponding to location 174 on the residual norm 170, modified basis functions are determined (e.g., as in FIG. 11A and 11B), and the modified basis functions are used for fitting (e.g., as in FIG. 11C) and the reconstruction (e.g., as in FIG. 11D).

Figure 12C:
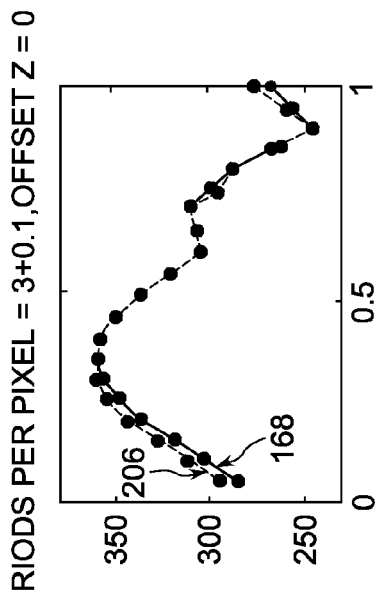
FIGS. 12A-D illustrate graphs corresponding to a third iteration of an embodiment of an offset stepping procedure.
Figure 12A:
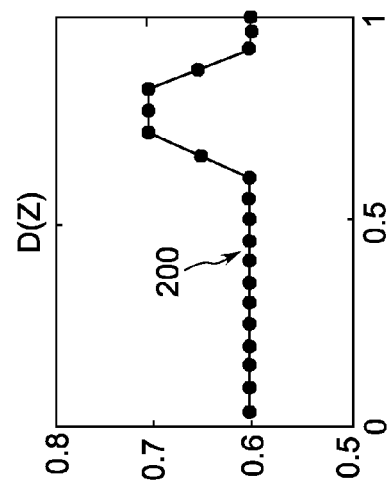
Figure 12D:
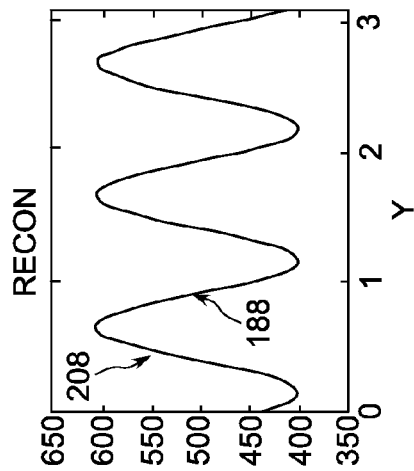
Figure 12B:
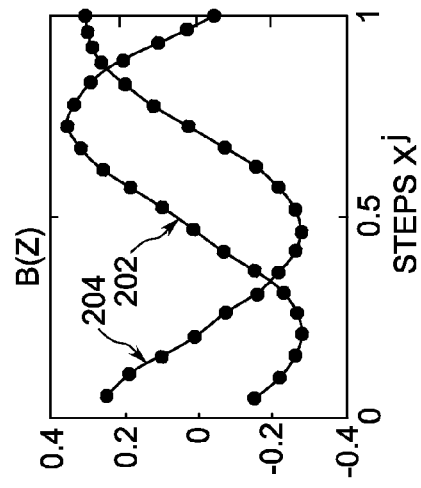

For further example, when the offset value corresponding to the minimum of the residual norm 170 is reached, the adaptive process enables identification of the correspondence between the sampled offset value and the minimum. For instance, this process is again repeated for the offset value corresponding to location 176 on the residual norm 170, as shown in FIGS. 12A-D. FIG. 12A illustrates a plot 200 of the basis function d for the z value corresponding to location 176 on the residual norm. FIG. 12B illustrates plots 202 and 204 of the real and imaginary parts of the basis function b, respectively, for the z value corresponding to location 176 on the residual norm. FIG. 12C illustrates the measured signal 168 and a computed fit 206 utilized to generate a NIF corrected reconstruction 208 that can be compared to the ground truth 188 in FIG. 12D. As shown, because the offset value corresponding to location 176 on the residual norm 170 corresponds to a minimum of the residual norm 170, the measured signal 168 and the fit 206 are substantial matches, and the NIF corrected reconstruction 208 and the ground truth 188 are also substantial matches. In this way, presently disclosed embodiments enable equation (12) to be solved for various offset sample values to determine the minimum residual norm.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for correcting for non-integer fringe fractions in differential phase contrast imaging, comprising:
   receiving data corresponding to a measured signal; wherein the measured signal corresponds to an X-ray signal detected by a detector after passing through a subject located with a grating arrangement between an X-ray source and the detector;
   determining a basis function in the Fourier domain based on an initial offset value;
   fitting the data corresponding to the measured signal to the basis function;
   determining an adapted basis function in the Fourier domain based on a shifted offset value; and
   fitting the data corresponding to the measured signal to the adapted basis function.

2. The method of claim 1, comprising determining which of the initial offset value and the shifted offset value corresponds to a minimum value of a residual norm function.

3. The method of claim 2, comprising reconstructing a phase image of the subject utilizing the one of the basis function and the adapted basis function that corresponds to the offset value corresponding to the minimum value of the residual norm function.

4. The method of claim 1, comprising determining a second basis function in the Fourier domain based on the initial offset value, fitting the data corresponding to the measured signal to the basis function and the second basis function, determining the adapted basis function and a second adapted basis function in the Fourier domain based on the shifted offset value, and fitting the data corresponding to the measured signal to the adapted basis function and the second adapted basis function.

5. The method of claim 4, comprising determining which of the initial offset value and the shifted offset value corresponds to a minimum value of a residual norm function.

6. The method of claim 5, comprising reconstructing a phase image of the subject utilizing one of a first basis function pair or a second basis function pair that corresponds to the offset value corresponding to the minimum value of the residual norm function, wherein the first basis function pair comprises the basis function and the second basis function, and the second basis function pair comprises the adapted basis function and the second adapted basis function 7. An X-ray imaging system for differential phase contrast imaging of a subject, comprising:
   an X-ray source that in operation generates an X-ray beam directed toward the subject;
   a detector that in operation detects at least a portion of the X-ray beam and produces a signal corresponding to the detected portion of the X-ray beam;
   a grating system comprising a source grating located between the X-ray source and the subject, and a phase grating and an analyzer grating each located between the subject and the detector;
   a controller that in operation receives the signal from the detector and performs a reconstruction of a phase image of the subject based on the signal, wherein the reconstruction comprises a fringe analysis in which the controller performs a non-integer fringe fraction correction utilizing one or more adapted basis functions in the Fourier domain.

8. The system of claim 7, wherein the non-integer fraction correction comprises determining an adapted basis function in the Fourier domain based on a shifted offset value and fitting the signal from the detector to the adapted basis function.

9. The system of claim 7, wherein the non-integer fraction correction comprises determining an offset value corresponding to an absolute minimum in a residual norm function by iteratively adapting the basis functions in the Fourier domain.

10. The system of claim 7, wherein in operation the controller generates a control signal that controls the analyzer grating to be shifted in a direction orthogonal to grating slits of the analyzer grating to a plurality of positions, and the detector detects at least a portion of the X-ray beam and produces a signal corresponding to the detected portion of the X-ray beam at each of the plurality of positions.

11. The system of claim 7, wherein the analyzer grating is located between the phase grating and the detector.

12. The system of claim 7, wherein the X-ray source comprises an incoherent X-ray source.

13. An image reconstruction method for differential phase contrast imaging, comprising:
   receiving data corresponding to a signal produced by an X-ray detector and corresponding to X-rays that passed through a subject and a grating system to reach the X-ray detector;
   performing a fringe analysis on the received data, wherein the fringe analysis comprises a non-integer fringe fraction correction utilizing one or more adapted basis functions in the Fourier domain to determine one or more Fourier coefficients; and
   generating a differential phase image of the subject by utilizing the one or more Fourier coefficients.

14. The method of claim 13, comprising integrating the differential phase image to produce a phase image of the subject.

15. The method of claim 13, comprising receiving second data corresponding to a second signal produced by an X-ray detector and corresponding to X-rays that passed through air and a grating system to reach the X-ray detector and utilizing the second data to generate the differential phase image.

16. The method of claim 13, wherein the non-integer fraction correction comprises determining the one or more adapted basis functions in the Fourier domain based on a shifted offset value.

17. The method of claim 16, wherein the non-integer fraction correction comprises fitting the data from the detector to the one or more adapted basis functions.

18. A non-transitory computer readable medium encoding one or more executable routines, which, when executed by a processor, cause the processor to perform acts comprising:
   performing an image reconstruction of a phase image of a subject based on a signal generated by an X-ray detector based on a detected X-ray beam that passed through a subject and a grating system, wherein performing the image reconstruction comprises a fringe analysis utilizing one or more adapted basis functions in the Fourier domain for a non-integer fringe fraction correction.

19. The computer readable medium of claim 18, wherein the non-integer fraction correction comprises determining an adapted basis function in the Fourier domain based on a shifted offset value and fitting the signal from the X-ray detector to the adapted basis function.

20. The computer readable medium of claim 18, wherein the non-integer fraction correction comprises determining an offset value corresponding to an absolute minimum in a residual norm function by iteratively adapting the basis functions in the Fourier domain.

\* \* \* \* \*